United States Patent [19]

Antonsson et al.

[11] 4,222,382
[45] Sep. 16, 1980

[54] FEMORAL COMPONENT HIP JOINT PROSTHESIS EXTRACTOR

[75] Inventors: Erik K. Antonsson, Vestal, N.Y.; Woodie C. Flowers, Auburndale, Mass.

[73] Assignee: Massachusetts Institute of Technology, Cambridge, Mass.

[21] Appl. No.: 6,699

[22] Filed: Jan. 26, 1979

[51] Int. Cl.³ .................. A61B 17/00; A61B 17/18
[52] U.S. Cl. .................. 128/303 R; 128/92 EC; 3/1.913
[58] Field of Search ............ 128/303 R, 92 EC, 92 E, 128/83, 92 C, 92 CA; 3/1.913, 1.91

[56] References Cited

U.S. PATENT DOCUMENTS

| 3,585,994 | 6/1971 | Huggler et al. | 128/303 R X |
| 3,801,989 | 4/1974 | McKee | 128/92 EC X |
| 3,818,514 | 6/1974 | Clark | 128/92 EC X |

OTHER PUBLICATIONS

Vitallium Surgical Appliances Catalog by Howmet Corp., New York, N. Y., 1964, p. 76, McReynolds Driver-Extractor Instrument, No. 6869.

Primary Examiner—Ronald L. Frinks
Attorney, Agent, or Firm—Arthur A. Smith, Jr.; Robert Shaw

[57] ABSTRACT

Extractor for removal of a femoral component of a total or partial hip joint reconstruction, in which an impact shock is applied directly through hardware to the extractor which is so shaped that converging jaws secure the neck of a prosthesis therein and the withdrawal shock is applied parallel to the stem of the prosthesis.

11 Claims, 5 Drawing Figures

FEMORAL COMPONENT HIP JOINT PROSTHESIS EXTRACTOR

The present invention relates to the surgical procedures involved in the removal of a femoral component of a total or partial hip joint reconstruction and, in particular, to extractors for the removal of a prosthesis which has been cemented with polymethylmethacrylate or the like into the proximal medullary cavity of the femur.

Current methods used to remove femoral components include that of grasping the neck of the prosthesis with pliers or a similar instrument and striking the side of the instrument with a hammer. Such primitive methods require the surgeon's hands as part of the system and are ineffective in that the hands absorb a high shock load of the impact of the hammer, and so transmit a very small part of the shock to the implanted prosthesis. Removal of an implant in polymethylmethacrylate requires a shock load to shear the cement at the interface between the implant prosthesis and the cement. Since the surgeons hands absorb much of the shock, less is transmitted to the cement, and removal is difficult. This also causes pain in the surgeon's hands.

It is the object of the invention to provide an effective mechanism for removal of a prosthesis previously implanted. Another object is to provide an effective mechanism such that the extraction requires a minimum of effort, can be performed quickly and is not painful to the operator.

These and still further objects are addressed hereinafter.

The foregoing objects are achieved, generally, in a prosthesis extractor for removing the femoral component of a hip-joint prosthesis having a head, a shoulder, with a neck therebetween, and a stem, which stem is elongate and shaped to the conform to the proximal medullary cavity of the femur within which the prosthesis is implanted; the prosthesis extractor has a base portion and a pair of spaced jaws, the jaws converging toward each other from a widely spaced region to a closely spaced region to form an opening sufficiently large to receive the head of the prosthesis and tapering so as to grasp the neck of the prosthesis therein, said jaws being angled with respect to said base portion to permit substantial alignment of forces applied by the extractor with the stem of the prosthesis. The prosthesis extractor, in an operative system, has attached to it an impact device which, typically, consists of a hammer or weight slidably disposed upon a shaft which has a stop at the end thereof to receive impact forces from the hammer. The shaft is attached to the extractor by a pivot joint that permits compensation for small amounts of misalignment between the shaft and the stem of the prosthesis—for forces to be proper, the two should be in alignment.

The invention is hereinafter described with reference to the accompanying drawing in which.

Figure 1:
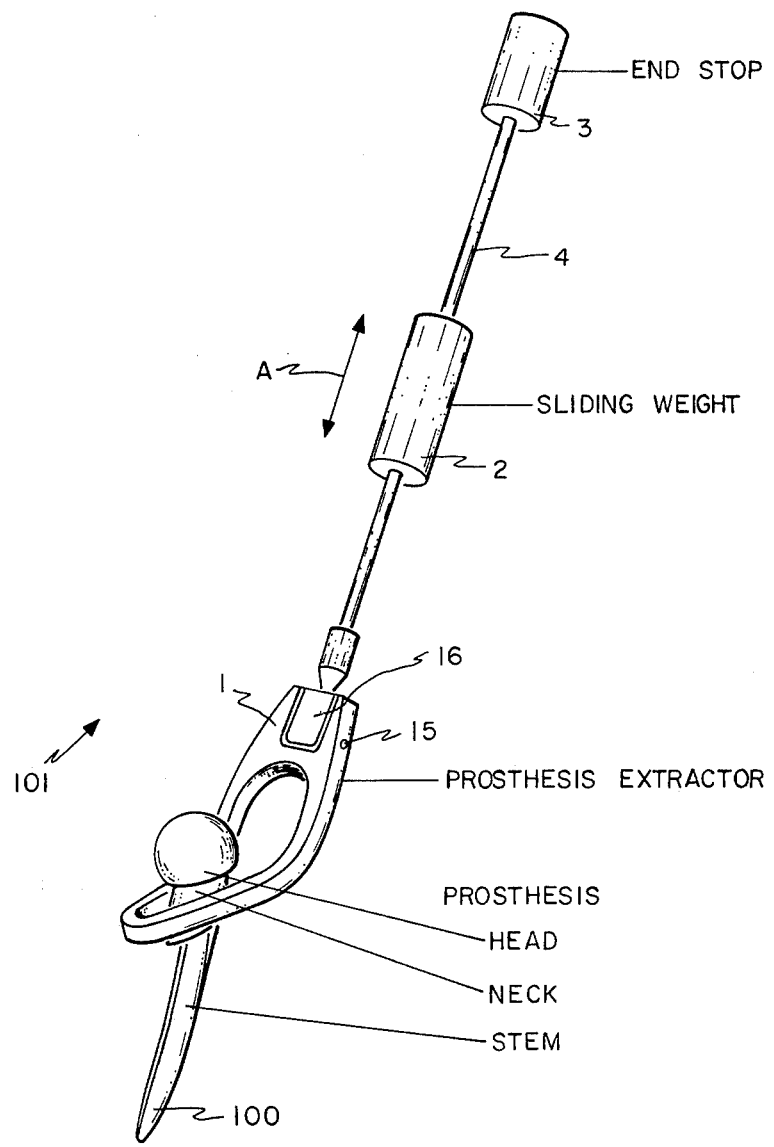
FIG. 1 is an isometric view of an assembly that includes a prosthesis extractor of the present invention in an assembly with other elements that interact therewith and a prosthesis.

Turning now to FIG. 1 there is shown at 101 an assembly or system for removing the femoral component labeled 100 of a total or partial hip reconstruction. The typical prosthesis 100 is cemented in a cavity in the femur, as is well known, and the function of the system 101 is to remove that prosthesis should trouble arise from the installation. To break the cement bond, it is necessary that a substantial outward impact shock be applied to the prosthesis and that shock, to be effective, it has been found for present purposes, must be one that is substantially aligned with the stem of the prosthesis.

Figure 5:
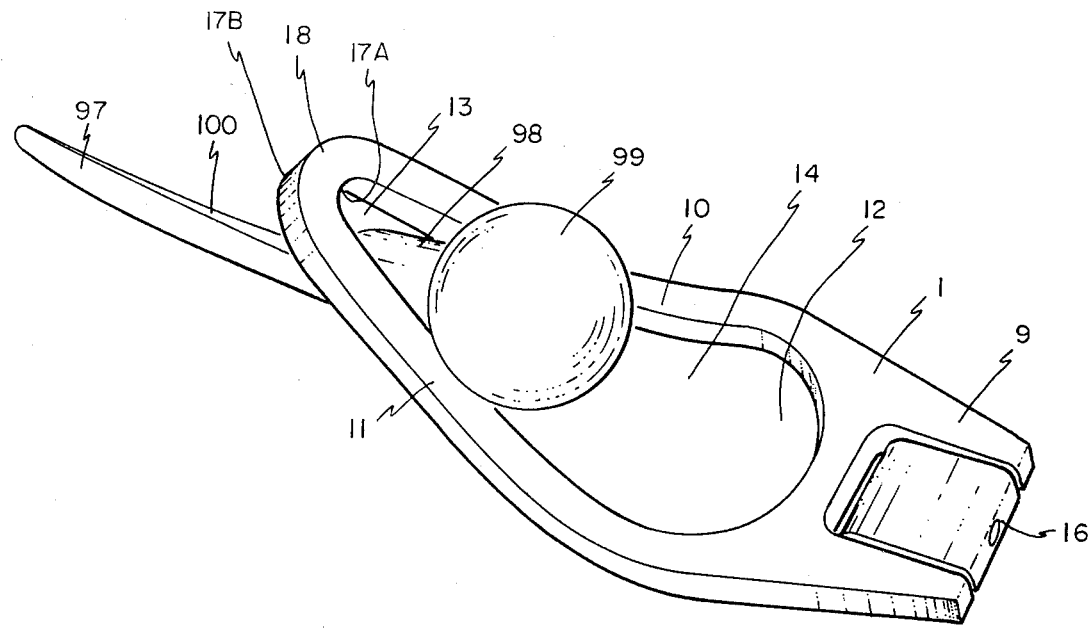
FIG. 5 is an isometric view showing the prosthesis extractor shown in FIGS. 2 and 3 and a prosthesis.
Figure 2:
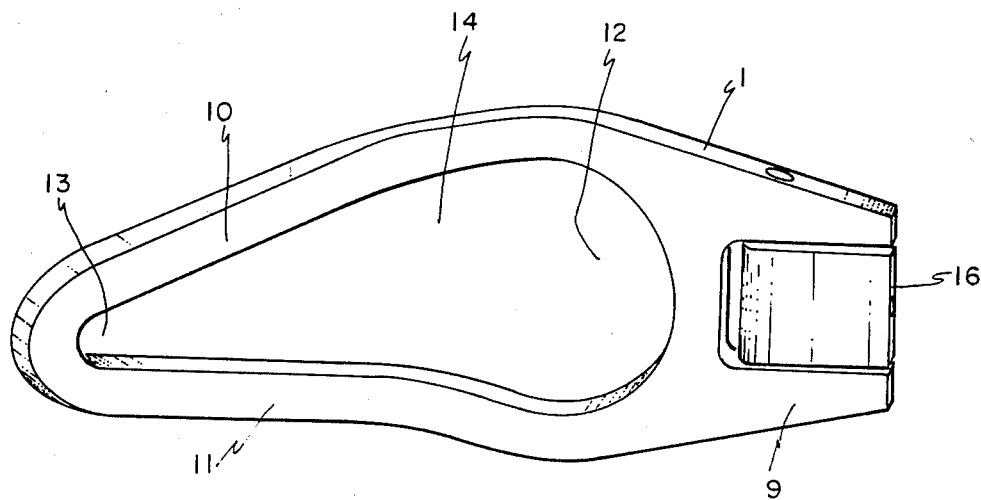
FIGS. 2 and 3 are respectively a top isometric view and a side isometric view of a prosthesis extractor, like the prosthesis extractor in FIG. 1.
Figure 3:
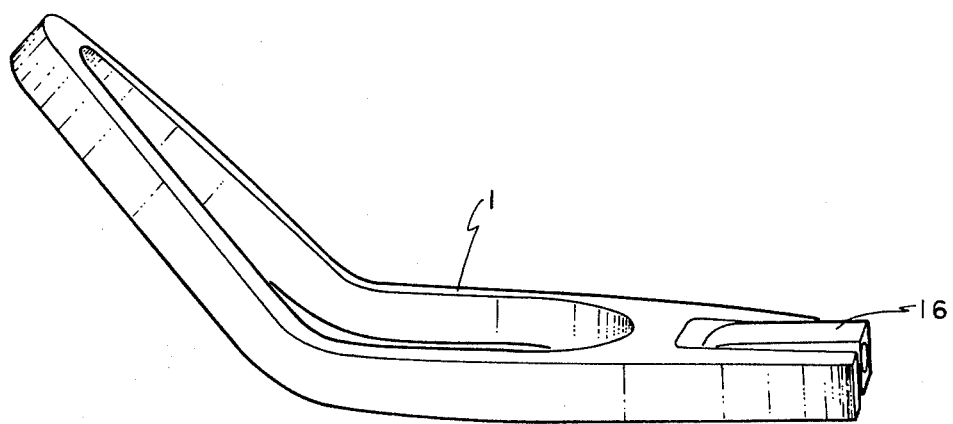

The system 101 includes a prosthesis extractor 1 which, as best shown in FIGS. 2 and 5 has a base portion 9 and a pair of spaced jaws 10 and 11 that converge toward each other from a widely-spaced region 12 to a closely-spaced region 13 to form an aperture 14 sufficiently large to receive the head labeled 99 of the prosthesis 100 in FIG. 5 and tapering, as shown, to grasp the neck shown at 98 of the prosthesis securely therein, the jaws 10 and 11 being angled (at an angle $\theta$ in FIG. 4) to the base portion to permit alignment of the stem designated 97 of the prosthesis with the elements of an impact device to apply the outward impact force properly.

The impact forces are applied by moving a sliding weight 2 that moves along a shaft or elongate portion 4 of the impact device up and down in FIG. 1 in the direction of the arrow marked A. Impact is thus effected between the sliding weight 2 and an end stop or anvil portion 3 of the impact device secured to the top of the shaft 4. The shaft 4 is attached to the extractor 1 by a pivotable joint 16 (see the pin labeled 15 in FIG. 1 which permits pivoting of the joint 16) that permits, upon impact, adjustment of alignment between the shaft 4 and the stem 97 to compensate for small misalignment therebetween to assure that the impact forces applied to the prosthesis 100 are properly directed. It has been found by the inventors that the angle $\theta$ is in the range from about 30° to 60°; in the actual extractor shown in FIGS. 2–5, the angle $\theta$ is 45°. The jaws 10 and 11 converge in the actual device at an angle of 25°, but a range from about 10° to about 30° is acceptable. The closely-spaced region 13 terminates in a curved end 17A in FIG. 5 having a small (0.2 inch) inner radius. The outside of the jaws or legs 10 and 11 converge in a radius that is small enough not to interfere with access to the prosthesis head 99, in vivo. In this same matter, the legs and the region of convergence thereof (i.e., the curved portion 18 between 17A and 17B in FIG. 5) must be sufficiently thin enough (~⅜ inch) that neither interferes with extraction. The joint 16 is threaded to accept a threaded shaft 4. The extractor 1 is formed of stainless steel or some other material which can be sterilized and which can withstand the large impact forces.

Figure 4:
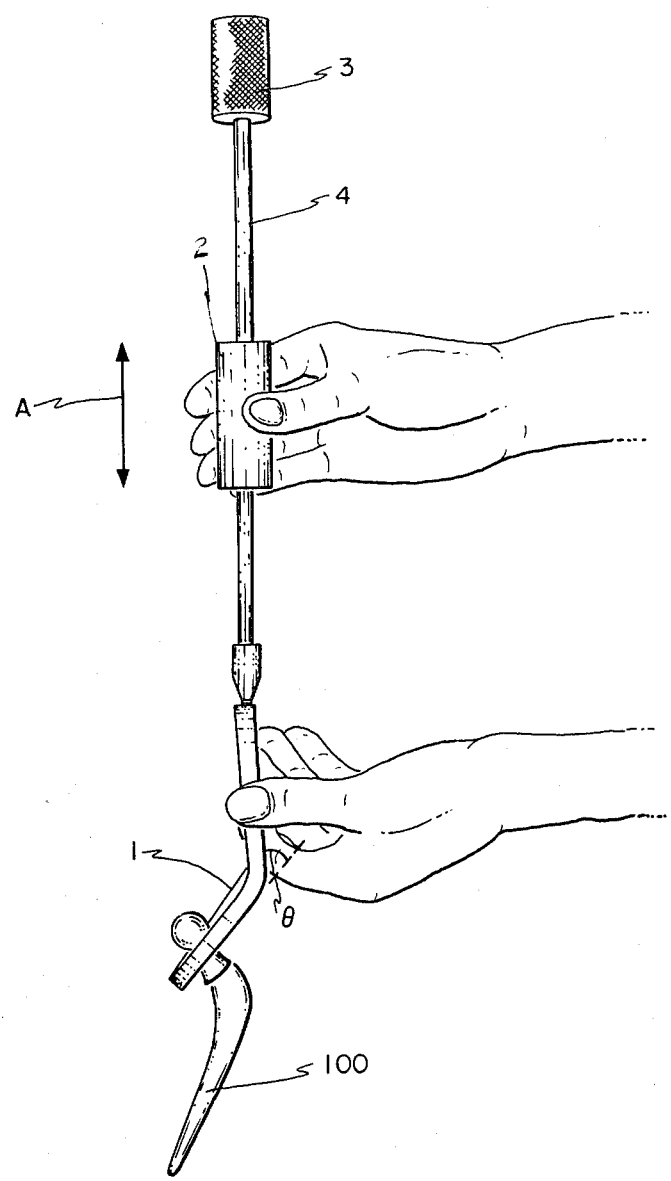
FIG. 4 is an elevation view of an assembly like the assembly of FIG. 1 and a prosthesis.

Removal procedure is depicted in FIG. 4 which shows two hands of an operator who secures the neck of the prosthesis in the tapered portion of the device and applies the necessary movement of the hammer or weight 2.

The prosthesis extractor 1 eliminates many of the problems of the previously used mechanisms for removing the femoral component of a hip-joint prosthesis and provides a relatively simple system, yet one that applies the necessary shock forces to dislodge such prosthesis. It is a relatively uncomplicated design, offers easy manipulation, sterilization, and so forth, and is adapted for use with existing impact-providing devices.

Further modifications of the invention herein disclosed will occur to persons skilled in the art and all such modifications are deemed to be within the spirit and scope of the invention as defined by the appended claims.

What is claimed is:

1. A prosthesis extractor comprising a base portion and a pair of spaced jaws, the jaws converging toward each other from a widely-spaced region to closely-spaced region to form an aperture sufficiently large to receive the head of a prosthesis and tapering so as to grasp the neck of the prosthesis securely therein, said jaw, being angled with respect to said base portion to permit the alignment of the stem of the prosthesis with the direction of applied force on the extractor.

2. Apparatus as claimed in claim 1 that includes an impact device connected to the prosthesis extractor, said impact device comprising an elongate portion and an anvil portion to receive impact to dislodge said prosthesis.

3. Apparatus as claimed in claim 2 wherein the prosthesis extractor is provided with means to attach the impact device thereto, said means to attach being secured to the base portion by a joint that permits relative rotation or pivoting therebetween.

4. Apparatus as claimed in claim 1 wherein the angle between the jaws and said base portion is in the range from about 30° to 60°.

5. Apparatus as claimed in claim 1 wherein the jaws converge at an angle in the range from about 10° to about 30°.

6. Apparatus as claimed in claim 1 wherein said aperture has rounded edges and terminates in a curved end having a small radius.

7. Apparatus as claimed in claim 1 in which the outside of the jaws which form the aperture converge in a radius that is small enough not to interfere with access to the prosthesis head, in vivo.

8. Apparatus as claimed in claim 1 wherein the jaws and the region of convergence are sufficiently thin that neither interferes with the extraction.

9. Apparatus as claimed in claim 1 wherein the base portion has an appropriately threaded portion to attach to an impact device.

10. Apparatus as claimed in claim 1 which is formed of material allowing sterilization thereof and is sufficiently strong to withstand substantial impact loads.

11. For removing the femoral component of a hip-joint prosthesis having a head, a shoulder, with a neck therebetween and a stem, which stem is elongate and shaped to the conform to the proximal medullary cavity of the femur within which the prosthesis is implanted, a prosthesis extract comprising a base portion and a pair of spaced jaws, the jaws converging toward each other from a widely spaced region to a closely spaced region to form an opening sufficiently large to receive the head of the prosthesis and tapering so as to grasp the neck of the prosthesis therein, said jaws being angled with respect to said base portion to permit substantial alignment of the jaws with the stem of the prosthesis.

* * * * *